United States Patent

Hamersma et al.

Patent Number: 5,292,878
Date of Patent: Mar. 8, 1994

[54] 17-SPIROFURAN-3'-YLIDENE STEROIDS

[75] Inventors: Johannes A. M. Hamersma; Everardus O. M. Orlemans, both of Oss, Netherlands

[73] Assignee: Akzo N.V., Arnhem, Netherlands

[21] Appl. No.: 994,039

[22] Filed: Dec. 21, 1992

[30] Foreign Application Priority Data

Dec. 20, 1991 [EP] European Pat. Off. ...... 91.203.366.9

[51] Int. Cl.$^5$ .................. C07J 21/00; A01K 31/56
[52] U.S. Cl. ................................................. 540/28
[58] Field of Search .................... 540/28; 514/178

[56] References Cited

U.S. PATENT DOCUMENTS 4,536,401 8/1985 Neef et al. .................. 514/173
4,900,725 2/1990 Nioue et al. .................. 514/173

FOREIGN PATENT DOCUMENTS 0116974 8/1984 European Pat. Off.
0321010 6/1985 European Pat. Off.
0289073 11/1988 European Pat. Off.
87/05908 1/1987 PCT Int'l Appl.

Primary Examiner—Paul J. Killos
Attorney, Agent, or Firm—William M. Blackstone

[57] ABSTRACT

The invention relates to an antiprogestin 17-spirofuran-3'-ylidene steroid having the formula

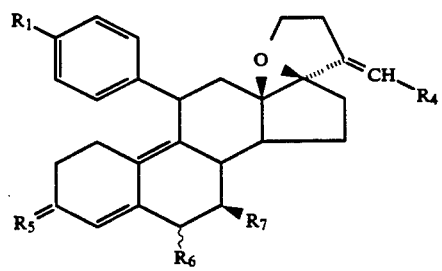

p0 $R_1$ is $NR_2R_3$, lower acyl, OH, SH, O-lower alkyl or $S(O)_n$-lower alkyl wherein n is 0-2;
$R_2$ and $R_3$ are independently selected from hydrogen and lower alkyl;
$R_4$ is hydrogen or lower alkyl;
$R_5$ is O, (H,H), (H,OH), (H,O-lower acyl), or NOH;
$R_6$ and $R_7$ are both hydrogen, or one is hydrogen and the other lower alkyl; and
the twitched line represents an α or β bond.

4 Claims, No Drawings

17-SPIROFURAN-3'-YLIDENE STEROIDS

The invention relates to novel 17-spirofuran-3'-ylidene steroids, to methods of preparation thereof, a pharmaceutical composition containing the same, and a use of these steroids for the manufacture of a medicament having antiprogestin activity.

Antiprogestins, i.e. compounds which show affinity for the progesterone receptor, are known. One of the best known compounds in this respect is RU 486, which is disclosed in European patent 0,057,115.

It has now been found that steroids having a 17-spirofuran-3'-ylidene ring show surprisingly strong affinity to the progesterone receptor, and, moreover, have at the same time decreased affinity to the glucocorticoid receptor. Further, the novel compounds have virtually no affinity to the mineralocorticoid receptor. The present steroids, therefore, show an improved selectivity and are more suitable for therapeutic use.

The 17-spirofuran-3'-ylidene steroids of the invention have a formula

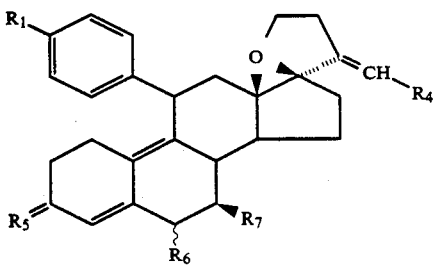

I wherein
$R_1$ is $NR_2R_3$, lower acyl, OH, SH, O-lower alkyl or $S(O)_n$-lower alkyl wherein n is 0–2;
$R_2$ and $R_3$ are independently selected from hydrogen and lower alkyl;
$R_4$ is hydrogen or lower alkyl;
$R_5$ is O, (H,H), (H,OH), (H,O-lower acyl), or NOH;
$R_6$ and $R_7$ are both hydrogen, or one is hydrogen and the other lower alkyl; and
the twitched line represents an α or β bond.

Preferred steroids according to the invention have formula I, wherein
$R_1$ is $N(CH_3)_2$, acetyl, S-lower alkyl, or $SO_2$-lower alkyl;
$R_4$ is hydrogen or methyl;
$R_5$ is O;
$R_6$ and $R_7$ are both hydrogen, or one is hydrogen and the other methyl.

Most preferred is the 17-spirofuran-3'-ylidene steroid, wherein $R_1$ is acetyl, $R_4$ is hydrogen, $R_5$ is O and $R_6$ and $R_7$ are both hydrogen.

The term lower alkyl means a branched or unbranched alkyl group having 1–66 carbon atoms, such as methyl, ethyl, propyl, isopropyl, butyl, tert-butyl, pentyl, hexyl and the like. Preferred alkyl groups have 1–4 carbon atoms, and most preferred is the methyl group.

The term lower acyl means an acyl group derived from an aliphatic carboxylic acid having 2–6 carbon atoms. Acetyl is the preferred acyl group.

When $R_4$ is an alkyl group Z- and E-isomers are possible. Both isomeric forms are considered to belong to this invention.

The 17-spirofuran-3'-ylidene steroids of this invention can be prepared in various ways. A convenient method is the cleavage of a protective group of a corresponding steroid in which the 3-keto or 3-oxim is protected, which steroid has the formula

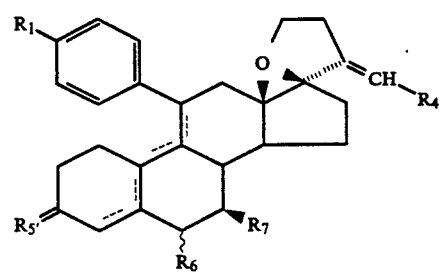

II wherein
$R_1$ is $NR_2R_3$, lower acyl, OH, SH, O-lower alkyl, or $S(O)_n$-lower alkyl wherein n is 0–2;
$R_2$ and $R_3$ are independently selected from hydrogen and lower alkyl;
$R_4$ is hydrogen or lower alkyl;
$R_5'$ is a protected O or protected NOH;
$R_6$ and $R_7$ are both hydrogen, or one is hydrogen and the other lower alkyl; the dotted line represents two conjugated bonds, and
the twitched line represents an α or β bond.

Suitable protective groups are known in the art, for instance, from T. W. Green: Protective Groups in Organic Synthesis (Wiley, NY, 1981), which is included by reference. Particularly suitable are acetals for the protection of keto groups, for example 1,2-ethylene ketal. In this respect, also a dithioketal should be mentioned, which easily can be converted into a keto group by treatment with silver nitrate.

Another suitable method is the dehydration of a compound having formula

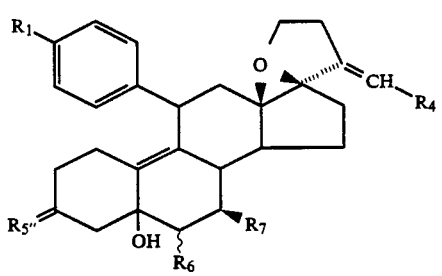

III wherein
$R_5''$ is protected O (H,H), (H,protected OH), (H,O-lower acyl), or protected NOH, and $R_1$–$R_4$, $R_6$–$R_7$, and the twitched line have the previously given meanings. The protective groups, if present, are simultaneously cleaved or cleaved after the dehydration step. Dehydration is normally performed under acidic conditions, but also catalytic dehydration (for example using aluminum oxide), and indirect dehydration by converting the 5-hydroxy group into a suitable leaving group, which is removed together with an adjacent hydrogen atom, are possible. An example of the latter method is the conversion of the 5-hydroxy group into a halogen like iodide, followed by dehydrohalogenation under alkaline conditions.

Yet another method is a Wittig, Wittig-like, or Peterson reaction using a compound having the formula

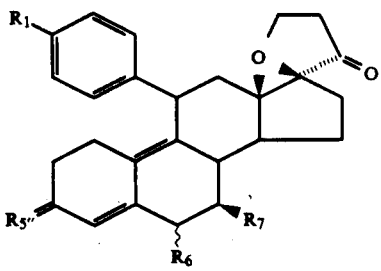

IV wherein $R_5''$ is protected O, (H,H), (H,protected OH), (H,O-lower acyl), protected NOH, and $R_1$-$R_3$, $R_6$-$R_7$, and the twitched line have the previously given meanings, and a $R_4$-$CH_2$-Wittig, $R_4$-$CH_2$-Wittig-like, or $R_4$-$CH_2$-Peterson reagent, wherein $R_4$ has the previously given meaning. This reaction is followed by deprotection of an optionally present protective group into the 17-spirofuran-3'-ylidene steroid of this invention. Suitable Wittig or Wittig-like reagents are triphenylphosphoranes such as $R_4$-$CH_2$-$P(Hal)Ph_3$, and the like, and suitable Peterson reagents are, for example, trimethylsilane regeants like $R_4$-$CH(MgHal)Si(Ch_3)_3$, wherein Hal denotes a halogen like chlorine or bromine.

Alternatively, the 17-spirofuran-3'-ylidene steroids of this invention can also be prepared by ring closure to the 17-spirofuran-3'-ylidene ring. In this method a compound having the formula

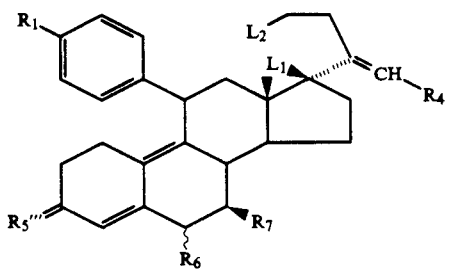

V wherein $R_5'''$ is $R_5$ or protected O, (H,H), (H,protected OH), or protected NOH, and $R_1$-$R_7$, and the twitched line have the previously given meanings, and one of $L_1$ and $L_2$ is OH and the other is a leaving group, is converted into a 17-spirofuran-3'-ylidene steroid, which after deprotection of an optionally present protective group affords the desired 17-spirofuran-3'-ylidene steroid. Leaving groups are known in the art. Suitable leaving groups are, for instance, hydroxy, halogen (particularly chlorine and bromine), and sulfonates such as paratoluene sulfonate and mesylate groups.

It is possible to convert the products obtained by one of the previously mentioned procedures into another product according to the invention. Using generally known methods it is, for instance, possible to convert steroids wherein $R_2$ and/or $R_3$ is hydrogen, for example, by a Leuckart-Wallach reaction, to afford steroids wherein $R_2$ and/or $R_3$ is alkyl. Steroids having $R_5$ is O can easily be converted into steroids having $R_5$ is NOH, for example, by condensation with hydroxylamine, or to steroids having $R_5$ is (H,OH), for example, by sodium borohydride reduction. Steroids having $R_5$ is (H,OH) can be acylated to steroids having $R_5$ is (H,O-lower acyl).

The compounds of the invention may be administered enterally or parenterally, and for humans preferably in a daily dosage of 0,001-10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray. For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

EXAMPLE 1

$(11\beta,17\alpha)$-17.23-epoxy-11-[(4-dimethylamino)phenyl]-19.24-dinorchola-4,9,20-trien-3-one a. To a solution of 25.6 g of $(17\beta)$-3-methoxyspiro-[estra-1,3,5(10)-triene-17,2'(3'H)-furan]-3'-one (see D. Gange and Ph. Magnus, J. Am. Chem. Soc., 100 (1978), 7746-7747) in 200 ml of ethanol and 200 ml of toluene were added 2.85 g of sodium borohydride, and the mixture was stirred at room temperature for 16 hours. Acetic acid was added until pH 7, followed by addition of water, and the mixture was extracted with toluene. Removal of the solvent under reduced pressure afforded the crude alcohol, which was crystallized from methanol to yield 24 g of $(17\beta, 3'S)$-4,,5,-dihydro-3-methoxyspiro[estra-1,3,5(10)-triene-17,2'(3'H)-furan]-3'-ol, m.p. 130° C.

b. (i) A solution of 9 g of $(17\beta, 3'S)$-4',5'-dihydro-3-methoxyspiro[estra-1,3,5(10)-triene-17,2'(3'H)-furan]-3'-ol in 150 ml of tetrahydrofuran was added to a solution of 4 g of lithium in 450 ml of liquid ammonia at −33° C. After stirring for 3 hours at this temperature 60 ml of ethanol were added and the ammonia was allowed to evaporate. The residue was partitioned between water and ethyl acetate. The organic layer was washed with brine, dried over magnesium sulfate and concentrated under reduced pressure, affording after trituration with diisopropyl ether 8.9 g of $(17\beta, 3'S)$-4',5'-dihydro-3-methoxyspiro[estra-2,5(10)-diene-17,2'(3'H)-furan]-3'-ol.

(ii) 8.9 g of the above-mentioned diene were dissolved in 65 ml of methanol and 65 ml of tetrahydrofuran. At 5° C. a solution of 4.6 g of oxalic acid in 45 ml of water and 22 ml of methanol was added. After stirring for 6 hours at ambient temperature the mixture was poured into an ice-cold 1% sodium hydrogen carbonate solution and extracted with ethyl acetate. The organic layer was washed with brine, dried over magnesium sulfate and concentrated under reduced pressure to give 8.5 g of the crude (17β, 3'S)-4',5'-dihydro-3'-hydroxyspiro[estr-5(10)-ene-17,2'(3'H)-furan]-3'-one.

(iii) 8.5 g of this ketone were dissolved in 90 ml of pyridine. To this solution were added portionwise 10 g of phenyltrimethylammonium tribromide during 15 min at 0° C. After stirring for 3 hours at room temperature the mixture was poured into 800 ml of ice-water and the product was extracted with ethyl acetate. The organic layer was washed with 2M hydrochloric acid, brine and dried over magnesium sulfate. The residue was chromatographed after evaporation of the solvent to yield 4.7 g of (17β, 3' S)-4', 5=-dihydro-3'-hydroxyspiro[estra-4,9-diene-17,2'(3'H)-furan]-3-one, m.p. 180° C.

c. (i) A mixture of 4.1 g of (17β, 3'S)-4',5'-dihydro-3'-hydroxyspiro[estra-4,9-diene-17,2'(3'H)-furan]-3-one, 30 ml of dichloromethane, 30 ml of ethylene glycol, 10 ml of triethyl orthoformate, and 200 mg of para-toluenesulphonic acid was stirred for 2 hours at room temperature. The reaction was stopped by the addition of water and sodium hydrogen carbonate, the layers were separated and the organic layer was washed with water. After drying over magnesium sulfate and concentration under reduced pressure 5.1 g of the crude (17β, 3'S) -4',5'-dihydro-3'-hydroxyspiro[estra-4,9-diene-17, 2'(3'H)-furan]-3-one 3-cyclic 1,2-ethanediyl acetal were obtained, which was used in the next step without further purification.

(ii) A mixture of 5.1 g of the above-mentioned compound, 200 ml of toluene, 36 ml of cyclohexanone and 3.6 g of aluminum iso-propoxide was refluxed for 3 hours. After cooling to room temperature, ethyl acetate was added and the mixture was washed repeatedly with a 75 % w/v solution of Seignette salt. The organic layer was washed with water, brine, and dried over magnesium sulfate. Evaporation of the solvent under reduced pressure followed by chromatography afforded 4 g of (17β) -4',5=-dihydrospiro[estra-5(10),9(11)-diene-17,2'(3'H)-furan]-3,3'-dione 3-cyclic 1,2-ethanediyl acetal, m.p. 146° C.

d. To a suspension of 3.09 g of methyltriphenylphosphonium bromide in 25 ml of toluene were added 0.83 g of potassium tert-butoxide. The mixture was refluxed for 45 min, and then cooled, after which a solution of 1.10 g of the acetal of c(ii) in 2 ml of toluene were added and the mixture was refluxed for 1 hour. The suspension was subsequently poured into ice-water, the toluene layer separated, washed with brine, dried over magnesium sulfate and concentrated under reduced pressure. The residue was chromatographed to afford 0.95 g of (17α)-17,23-epoxy-19,24-dinorchola -5(10),9(11),20-trien-3-one 3-cyclic 1,2-ethanediyl acetal, m.p. 132 ° C.

e. (i) To a solution of 3.7 g of 17α)-17,23-epoxy-19,24-dinorchola-5(10),9(11),20-trien-3-one 3-cyclic 1,2-ethanediyl acetal in 25 ml of dichloromethane were added 5 g of sodium hydrogen carbonate. To this mixture was added at −40° C. a solution of 2.5 g of meta-chloroperbenzoic acid in 15 ml of dichloromethane. After stirring for 30 min at 0° C., the mixture was poured into ice-water and extracted with dichloromethane. The organic layer was washed with a sodium hydrogen carbonate solution and with water, dried over magnesium sulfate and concentrated under reduced pressure. The residue was chromatographed to give 1.8 g of the intermediate 5α, 10α-epoxide.

(ii) To a solution of [4-N,N-(dimethylamino)phenyl]-magnesium bromide (prepared from 4.4 g of 4-bromo-N,N-dimethylaniline and 0.6 g of magnesium) in 40 ml of tetrahydrofuran were added 0.5 g of copper(I) chloride at room temperature. Subsequently, 1.8 g of the 5α, 10α-epoxide of e(i) in 10 ml of tetrahydrofuran were added and stirring was continued for 30 min. The mixture was poured into an ammonium chloride solution and extracted with ethyl acetate. After washing with water, the organic layer was dried over magnesium sulfate and concentrated under reduced pressure. The residue was chromatographed to afford 1.4 g of the intermediate (5α, 11β, 17α)-17,23-epoxy-5-hydroxy-11-[(4-dimethylamino)phenyl]-19,24-dinorchola-9,20-dien-3-one 3-cyclic 1,2-ethanediyl acetal.

(iii) 1.4 g of the acetal of e(ii) in 15 ml of 70% acetic acid were heated for 2 hours at 50 ° C. After cooling to room temperature the mixture was neutralized with sodium hydrogen carbonate and extracted with ethyl acetate. After drying over magnesium sulfate, the solvent was evaporated and the residue chromatographed to give 0.9 g of (11β, 17α)-17,23-epoxy-11-[(4-dimethylamino)phenyl]-19,24-dinorchola-4,9,20-trien-3-one, m.p. 168° C., $[\alpha]_D^{20} = +125°$ (c =1.135, dioxane).

EXAMPLE 2

In an analogous manner as described in Example 1 were prepared:

(7β,11β,17α)-17,23-epoxy-7-methyl-11-[(4-dimethylamino) -phenyl]-19,24-dinorchola-4,9,20-triene-3-one, m.p. 100° C., $[\alpha]_D^{20} = +368°$ (c =1.02, dioxane).

(11β, 17α)-11-(4-acetylphenyl)-17,23-epoxy-19,24-dinorchola -4,9,20-trien-3-one, m.p. 126° C., $[\alpha]_D^{20} = +82°$ (c =0.955, dioxane).

(11β, 17α)-11-(4-methoxyphenyl)-17,23-epoxy-19,24-dinorchola-4,9,20-trien-3-one, m.p. 185 ° C.

(6β, 11β, 17α)-17,23-epoxy-6-methyl-11-(4-dimethyl -aminophenyl)-19,24-dinorchola-4,9,20-trien-3-one, m.p. 89° C., $[\alpha]_D^{20} = +128°$ (c =1.03, dioxane).

(11β, 17α)-17,23-epoxy-11-(4-ethenylphenyl)-19,24-dinorchola -4,9,20-trien-3-one. m.p. 191° C.; $[\alpha]_D^{20} = +128°$ (c =0.94, dioxane).

(11β. 17α)-17,23-epoxy-11-(4-methylthiophenyl)-19,24-dinorchola -4,9,20-trien-3-one. m.p. 186° C.; $[\alpha]_D^{20} = +121°$ (c =1.155, dioxane).

The E and Z-ethylidene derivatives were prepared analogously to the preparation of (11β, 17α)-11-[(4-dimethylamino)phenyl]-17,23-epoxy-19,24-dinorchola -4,9,20-trien-3-one by using ethyl triphenylphosphonium bromide. Separation by chromatography afforded: (3'E,11β,17β)-11-[(4-dimethylamino)phenyl]-3'-ethylidene -4',5'-dihydrospiro[estra-4,9-diene-17,2'(3'H)-furan]-3-one. m.p. 175° C.; $[\alpha]_D^{20} = +128°$ (c =0.885, dioxane).

(3'Z,11β, 17β)-11-[(4-dimethylamino)phenyl]-3'-ethylidene -4',5'-dihydrospiro[estra-4,9-diene-17,2'(3'H)-furan]-3-one. m.p. 172° C.

EXAMPLE 3

The intermediate of Example 1d can also be prepared by treatment of (17β)-4',5'-dihydrospiro[estra-5(10),9(11) -diene-17,2'(3'H)-furan]-3,3'-dione 3-cyclic 1,2-ethanediyl acetal with trimethylsilylmethylmagnesium chloride, followed by acid treatment.

EXAMPLE 4

The intermediate of Example 1c(ii) can also be prepared by converting the known estra-5(10),9(11)-dien-3,17-dione 3-cyclic 1,2-ethanediyl acetal (A. Belanger, D. Philibert, and G. Teutsch, Steroids, 37 (1981), 361–383) in a similar manner as described by D. Gange and Ph. Magnus, J. Am. Chem. Soc., 100 (1978), 7747–7748:

(i) To 65 ml of n-butyllithium (1.6M solution in hexane) in 48 ml of tetrahydrofuran were added 9.3 ml of 1-methoxy-1,2-propadiene at −78° C. After stirring for 45 min at this temperature 10.6 g of estra-5(10),9(11)-diene-3,17-dione 3-cyclic 1,2-ethanediyl acetal were added. Subsequently, the mixture was stirred at −40° C. for 30 min and poured into an ice-cold ammonium chloride solution. Ethyl acetate was added and the layers were separated. The organic layer was washed with brine, dried over magnesium sulfate and the solvent was removed under reduced pressure.

(ii) The crude 1,2-propadiene was mixed with 230 ml of tert-butanol, 3.75 g of potassium tert-butoxide and 0.3 g of dicyclohexano-18-crown-6. After refluxing for 8 hours, the mixture was poured into water and extracted with ethyl acetate. The organic layer was dried over magnesium sulfate, evaporated, and the residue was chromatographed to afford 9.1 g of the methyl enol ether of (17β)-4',5'-dihydrospiro[estra -5(10),9(11)-diene-17,2'(3'H)-furan]-3,3'-dione 3-cyclic 1, 2-ethanediyl acetal.

(iii) This enol ether was dissolved in 70 ml of acetone and a 1M hydrochloric acid solution was added until pH 2. The mixture was stirred for 3 h, subsequently poured into a sodium hydrogen carbonate solution, and extracted with ethyl acetate. After drying over magnesium sulfate and removal of the solvent, the residue was subjected to chromatography to yield 6.4 g of (17β)-4',5'-dihydro-spiro[estra-5(10),9(11) -diene-17,2'(3'H)-furan]-3,3'-dione 3-cyclic 1,2-ethanediyl acetal.

EXAMPLE 5

The intermediate of Example 1d can also be prepared in one step by reaction of estra-5(10),9(11)-dien-3,17-dione 3-cyclic 1,2-ethanediyl acetal with 4-chloro-2lithio-1-butene. Finally introduction of the 20–21 double bond into the cholane system could also be effected by an elimination reaction of an (17α, 20xi) -17,23-epoxy-24-norcholane precursor possessing a suitable leaving group in either the 20- or the 21-position.

EXAMPLE 6

(i) 520 mg of (5α, 11β, 17α)-17,23-epoxy-5-hydroxy-11-[(4-(methylthio)phenyl]-19,24-dinorchola-9,20-dien-3-one 3-cyclic 1,2-ethanediyl acetal [prepared analogously to EXAMPLE 2e(ii)], 5 ml of acetone and 0.1 ml of 30% hydrogen peroxide were refluxed for 2 h. After cooling to room temperature, water was added and the mixture was extracted with ethyl acetate. The organic layer was washed with a sodium thiosulfate solution and with water, dried over magnesium sulfate and concentrated under reduced pressure.

(ii) The residue (515 mg) was dissolved in 5 ml of 70% acetic acid and heated for 3 h at 50° C. After cooling to room temperature water was added and the mixture was neutralized with sodium hydrogen carbonate and extracted with ethyl acetate. After drying over magnesium sulfate the solution was filtered over silicagel to give 250 mg of a mixture of diastereomeric sulfoxides of (11β, 17α)-17,23-epoxy-11-[4-(methylsulfinyl)-phenyl]-19,24-dinorchola-4,9,20-trien-3-one. m.p. 115° C.

EXAMPLE 7

(i) To a solution of 520 mg of a diastereomeric mixture of (5α, 11β, 17α)-17,23-epoxy-5-hydroxy-11-[(4-(methyl-sulfinyl)phenyl]-19,24-dinorchola-9,20-dien-3-one 3-cyclic 1,2-ethanediyl acetal [EXAMPLE 6(i)], in 5 ml of methyl alcohol was added at 5° C. a solution of 615 mg of oxone (KHSO$_5$) in 6 ml of water. After stirring for 3 h at this temperature the mixture was extracted with dichloromethane. The organic layer was washed with water, dried over magnesium sulfate and concentrated under reduced pressure.

(ii) The residue (520 mg) was dissolved in 5 ml of 70% acetic acid and heated for 3 h at 50° C. After cooling to room temperature the mixture was neutralized with sodium hydrogen carbonate and extracted with ethyl acetate. After drying over magnesium sulfate the solvent was removed and the residue was chromatographed to give 510 mg of (11β, 17α)-17,23-epoxy-11-[4-(methylsulfonyl)phenyl]-19,24-dinorchola-4,9,20-trien-3-one. m.p. 142° C.

We claim:

1. A 17-spirofuran-3'-ylidene steroid having the formula

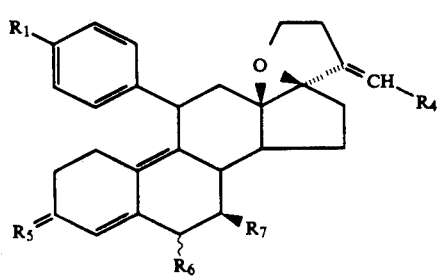

I wherein
R$_1$ is NR$_2$R$_3$, lower acyl, OH, SH, O-lower alkyl, or S(O)$_n$-lower alkyl wherein n is 0–2;
R$_2$ and R$_3$ are independently selected from hydrogen and lower alkyl;
R$_4$ is hydrogen or lower alkyl;
R$_5$ is O, (H,H), (H,OH), (H,O-lower acyl), or NOH;
R$_6$ and R$_7$ are both hydrogen, or one is hydrogen and the other lower alkyl; and
the twitched line represents an α or β bond.

2. The 17-spirofuran-3'-ylidene steroid of claim 1, wherein
R$_1$ is N(CH$_3$)$_2$, acetyl, S-lower alkyl, or SO$_2$-lower alkyl;
R$_4$ is hydrogen or methyl;
R$_5$ is O;
R$_6$ and R$_7$ are both hydrogen, or one is hydrogen and the other methyl.

3. The 17-spirofuran-3'-ylidene steroid of claim 2, wherein R$_1$ acetyl, R$_4$ is hydrogen, R$_5$ is O, R$_6$ and R$_7$ are both hydrogen.

4. A pharmaceutical composition comprising the 17-spirofuran-3'-ylidene steroid of claim 1 in an effective amount for effecting antiprogestin activity and pharmaceutically acceptable auxiliaries.

* * * * *